(12) United States Patent
Sirhan et al.

(10) Patent No.: US 7,018,405 B2
(45) Date of Patent: *Mar. 28, 2006

(54) INTRAVASCULAR DELIVERY OF METHYLPREDNISOLONE

(75) Inventors: Motasim Sirhan, Sunnyvale, CA (US); John Yan, Los Gatos, CA (US)

(73) Assignee: Avantec Vascular Corporation, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/782,804

(22) Filed: Feb. 13, 2001

(65) Prior Publication Data

US 2002/0082677 A1 Jun. 27, 2002

Related U.S. Application Data

(60) Provisional application No. 60/258,024, filed on Dec. 22, 2000.

(51) Int. Cl.
*A61F 2/06* (2006.01)

(52) U.S. Cl. .................. 623/1.42; 623/1.45

(58) Field of Classification Search ........... 623/1.42, 623/1.43, 1.44, 1.45, 1.46, 1.47, 1.48
See application file for complete search history.

(56) References Cited

U.S. PATENT DOCUMENTS

| | | | |
|---|---|---|---|
| 3,976,071 A | 8/1976 | Sadek | |
| 3,993,749 A | 11/1976 | Sehgal et al. | |
| 4,810,524 A | 3/1989 | Nakayama et al. | |
| 4,832,686 A | 5/1989 | Anderson | |
| 4,883,666 A | 11/1989 | Sabel et al. | |
| 4,894,231 A | 1/1990 | Moreau et al. | |
| 4,897,268 A | 1/1990 | Tice et al. | |
| 4,921,723 A | 5/1990 | Nichols et al. | |
| 5,024,671 A | 6/1991 | Tu et al. | |

(Continued)

FOREIGN PATENT DOCUMENTS

EP 063 365 B1 9/1985

(Continued)

OTHER PUBLICATIONS

Rajasubramanian et al., "Fabrication of resorbable microporus intravasular stents for gene therapy applications" *ASAIO Journal*, 40:M584-589 (1994).

(Continued)

*Primary Examiner*—Corrine McDermott
*Assistant Examiner*—Hieu Phan
(74) *Attorney, Agent, or Firm*—Townsend and Townsend and Crew LLP

(57) ABSTRACT

The present invention provides improved devices and methods for minimizing and/or inhibiting restenosis and hyperplasia after intravascular intervention. In particular, the present invention provides luminal prostheses which allow for programmed and controlled methylprednisolone delivery with increased efficacy to selected locations within a patient's vasculature to inhibit restenosis. An intraluminal delivery prosthesis may comprise an expansible structure and means on or within the structure for releasing methylprednisolone into the body lumen to inhibit smooth muscle cell proliferation.

28 Claims, 7 Drawing Sheets

U.S. PATENT DOCUMENTS

| | | | |
|---|---|---|---|
| 5,067,491 A | 11/1991 | Taylor, II et al. | |
| 5,112,457 A | 5/1992 | Marchant | |
| 5,163,952 A | 11/1992 | Froix | |
| 5,176,907 A | 1/1993 | Leong | |
| 5,283,257 A * | 2/1994 | Gregory et al. | 514/458 |
| 5,286,254 A | 2/1994 | Shapland et al. | |
| 5,342,348 A | 8/1994 | Kaplan | |
| 5,355,832 A | 10/1994 | Loh et al. | |
| 5,356,433 A | 10/1994 | Rowland et al. | |
| 5,411,550 A | 5/1995 | Herweck et al. | |
| 5,419,760 A | 5/1995 | Narcisco, Jr. | |
| 5,447,724 A | 9/1995 | Helmus et al. | |
| 5,447,799 A | 9/1995 | Loh et al. | |
| 5,463,010 A | 10/1995 | Hu et al. | |
| 5,464,450 A | 11/1995 | Buscemi et al. | |
| 5,464,650 A | 11/1995 | Berg et al. | |
| 5,474,563 A | 12/1995 | Myler et al. | |
| 5,484,584 A | 1/1996 | Wallace et al. | |
| 5,500,013 A | 3/1996 | Buscemi et al. | |
| 5,512,055 A * | 4/1996 | Domb et al. | 128/207.14 |
| 5,516,781 A | 5/1996 | Morris et al. | |
| 5,543,158 A | 8/1996 | Gref et al. | |
| 5,545,208 A | 8/1996 | Wolff et al. | |
| 5,551,954 A | 9/1996 | Buscemi et al. | |
| 5,563,146 A | 10/1996 | Morris et al. | |
| 5,569,463 A | 10/1996 | Helmus et al. | |
| 5,591,227 A | 1/1997 | Dinh et al. | |
| 5,609,629 A | 3/1997 | Fearnot et al. | |
| 5,624,411 A | 4/1997 | Tuch | |
| 5,637,113 A | 6/1997 | Tartaglia et al. | |
| 5,646,160 A | 7/1997 | Morris et al. | |
| 5,649,977 A | 7/1997 | Campbell | |
| 5,656,297 A | 8/1997 | Bernstein et al. | |
| 5,665,728 A | 9/1997 | Morris et al. | |
| 5,679,400 A | 10/1997 | Tuch | |
| 5,700,286 A | 12/1997 | Tartaglia et al. | |
| 5,725,567 A | 3/1998 | Wolff et al. | |
| 5,735,811 A | 4/1998 | Brisken | |
| 5,769,883 A | 6/1998 | Buscemi et al. | |
| 5,769,884 A | 6/1998 | Solovay | |
| 5,824,049 A | 10/1998 | Ragheb et al. | |
| 5,837,008 A | 11/1998 | Berg et al. | |
| 5,843,172 A | 12/1998 | Yan | |
| 5,851,231 A | 12/1998 | Wolff et al. | |
| 5,876,452 A | 3/1999 | Athanasiou et al. | |
| 5,879,808 A | 3/1999 | Wary et al. | |
| 5,891,108 A | 4/1999 | Leone et al. | |
| 5,893,840 A | 4/1999 | Hull et al. | |
| 5,951,586 A | 9/1999 | Berg et al. | |
| 5,958,510 A | 9/1999 | Sivaramakrishnam et al. | |
| 5,968,092 A | 10/1999 | Buscemi et al. | |
| 5,972,027 A | 10/1999 | Johnson | |
| 5,980,551 A | 11/1999 | Summers et al. | |
| 5,980,566 A | 11/1999 | Alt et al. | |
| 5,997,468 A | 12/1999 | Wolff et al. | |
| 6,051,276 A | 4/2000 | Wary et al. | |
| 6,054,122 A | 4/2000 | MacPhee et al. | |
| 6,063,101 A | 5/2000 | Jacobsen et al. | |
| 6,071,305 A | 6/2000 | Brown et al. | |
| 6,086,952 A | 7/2000 | Lang et al. | |
| 6,096,070 A | 8/2000 | Ragheb et al. | |
| 6,099,561 A | 8/2000 | Alt | |
| 6,153,252 A | 11/2000 | Hossainy et al. | |
| 6,183,507 B1 | 2/2001 | Lashinski et al. | |
| 6,197,013 B1 | 3/2001 | Reed et al. | |
| 6,203,536 B1 | 3/2001 | Berg et al. | |
| 6,240,616 B1 | 6/2001 | Yan | |
| 6,253,443 B1 | 7/2001 | Johnson | |
| 6,273,908 B1 | 8/2001 | Ndondo-Lay | |
| 6,273,913 B1 | 8/2001 | Wright et al. | |
| 6,287,628 B1 | 9/2001 | Hossainy et al. | |
| 6,299,604 B1 | 10/2001 | Ragheb et al. | |
| 6,395,326 B1 | 5/2002 | Castro et al. | |
| 6,471,980 B1 | 10/2002 | Sirhan et al. | |
| 6,506,437 B1 * | 1/2003 | Harish et al. | 427/2.25 |
| 2001/0027340 A1 | 10/2001 | Wright et al. | |
| 2001/0029351 A1 | 10/2001 | Falotico et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0016625 A1 | 2/2002 | Falotico et al. | |
| 2002/0032414 A1 | 3/2002 | Ragheb et al. | |

FOREIGN PATENT DOCUMENTS

| | | |
|---|---|---|
| EP | 184 162 B1 | 4/1994 |
| EP | 0 923 953 A2 | 6/1999 |
| EP | 0950386 A2 | 10/1999 |
| EP | 0950386 A3 | 10/1999 |
| EP | 1277449 A | 1/2003 |
| WO | WO 90/13332 | 11/1990 |
| WO | WO 98/36784 A1 | 8/1998 |
| WO | WO 00/10622 A1 | 3/2000 |
| WO | WO 01/01957 | 1/2001 |
| WO | WO 01/41678 | 6/2001 |
| WO | WO 02/083039 A | 10/2002 |

OTHER PUBLICATIONS

U.S. Appl. No. 09/783,253, filed Feb. 13, 2001, entitled "Apparatus and methods for controlled substance delivery from implanted prosthesis".

U.S. Appl. No. 09/783,254, filed Feb. 13, 2001, entitled Intravascular delivery of mizorbine.

U.S. Appl. No. 09/782,927, filed Feb. 13, 2001, entitled Intravascular delivery of mycophenolic acid.

* cited by examiner

INTRAVASCULAR DELIVERY OF METHYLPREDNISOLONE

CROSS-REFERENCES TO RELATED APPLICATIONS

This application claims the benefit of Provisional Application No. 60/258,024, filed Dec. 22, 2000, under 37 C.F.R. §1.78(a)(3), the full disclosure of which is incorporated herein by reference.

BACKGROUND OF THE INVENTION

1. Field of the Invention

The present invention relates generally to medical devices and methods. More particularly, the present invention provides luminal prostheses, such as vascular stents and grafts, which allow for controlled substance delivery for inhibiting restenosis in a blood vessel following balloon angioplasty or other interventional treatments.

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expansible distal end usually in the form of an inflatable balloon, is positioned in the blood vessel at the stenotic site. The expansible end is expanded to dilate the vessel to restore adequate blood flow beyond the diseased region. Other procedures for opening stenotic regions include directional arthrectomy, rotational arthrectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the frequent occurrence of restenosis.

Restenosis refers to the re-narrowing of an artery after an initially successful angioplasty. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat PTA or other procedure to alleviate the restenosis.

A number of strategies have been proposed to treat hyperplasia and reduce restenosis. Previously proposed strategies include prolonged balloon inflation during angioplasty, treatment of the blood vessel with a heated balloon, treatment of the blood vessel with radiation following angioplasty, stenting of the region, and other procedures. While these proposals have enjoyed varying levels of success, no one of these procedures is proven to be entirely successful in completely avoiding all occurrences of restenosis and hyperplasia.

As an alternative or adjunctive to the above mentioned therapies, the administration of therapeutic agents following PTA for the inhibition of restenosis has also been proposed. Therapeutic treatments usually entail pushing or releasing a drug through a catheter or from a stent. Of particular interest herein, stents may incorporate a biodegradable or nondegradable matrix to provide programmed or controlled release of therapeutic agents within a blood vessel. Biodegradable or bioerodible matrix materials employed for controlled release of drugs may include poly-l-lactic acid/poly-e-caprolactone copolymer, polyanhydrides, polyorthoesters, polycaprolactone, poly vinyl acetate, polyhydroxybutyrate/polyhyroxyvalerate copolymer, polyglycolic acid, polyactic/polyglycolic acid copolymers and other aliphatic polyesters, among a wide variety of polymeric substrates employed for this purpose.

While holding great promise, the delivery of therapeutic agents for the inhibition of restenosis has not been entirely successful. In particular, the release of drugs from stents has often been characterized by inconsistent and/or ineffective results because therapeutic agents are often released before they are needed, i.e., before hyperplasia and endothelialization begin. Drug delivery before any cellular or endothelial formation may also pose serious dangers, especially when dealing with the delivery of certain toxic agents. Furthermore, a rapid initial release of drugs causes delayed endothelialization and/or enlargement of the vessel wall, as a substantial number of cells are killed with increased drug loading. The use of drug release matrices can ameliorate the rapid release problems but do not provide programmed time-delay to impact restenosis at the onset of hyperplasia.

For these reasons, it would be desirable to provide improved devices and methods for reducing and/or inhibiting restenosis and hyperplasia following angioplasty and other interventional treatments. In particular, it would be desirable to provide improved devices and methods, utilizing luminal prostheses, such as vascular stents and grafts, which provide programmed and controlled substance delivery with increased efficacy to inhibit restenosis. It would further be desirable to provide such devices and methods which would reduce and/or further eliminate drug washout and potentially provide minimal to no hindrance to endothelialization of the vessel wall. At least some of these objectives will be met by the devices and methods of the present invention described hereinafter.

2. Description of the Background Art

Method and apparatus for releasing active substances from implantable and other devices are described in U.S. Pat. Nos. 6,096,070; 5,824,049; 5,624,411; 5,609,629; 5,569,463; 5,447,724; 5,464,650; and 5,283,257. The use of stents for drug delivery within the vasculature are described in PCT Publication No. WO 01/01957 and U.S. Pat. Nos. 6,099,561; 6,071,305; 6,063,101; 5,997,468; 5,980,551; 5,980,566; 5,972,027; 5,968,092; 5,951,586; 5,893,840; 5,891,108; 5,851,231; 5,843,172; 5,837,008; 5,769,883; 5,735,811; 5,700,286; 5,679,400; 5,649,977; 5,637,113; 5,591,227; 5,551,954; 5,545,208; 5,500,013; 5,464,450; 5,419,760; 5,411,550; 5,342,348; 5,286,254; and 5,163,952. Biodegradable materials are described in U.S. Pat. Nos. 6,051,276; 5,879,808; 5,876,452; 5,656,297; 5,543,158; 5,484,584; 5,176,907; 4,894,231; 4,897,268; 4,883,666; 4,832,686; and 3,976,071. The use of hydrocylosiloxane as a rate limiting barrier is described in U.S. Pat. No. 5,463,010. Methods for coating of stents is described in U.S. Pat. No. 5,356,433. Coatings to enhance biocompatibility of implantable devices are described in U.S. Pat. Nos. 5,463,010; 5,112,457; and 5,067,491.

The disclosure of this application is related to the disclosures of the following applications being filed on the same day: Ser. Nos. 09/783,253; 09/782,927; and 09/783,254.

The full disclosures of each of the above references are incorporated herein by reference.

SUMMARY OF THE INVENTION

The present invention provides improved devices and methods for inhibiting restenosis and hyperplasia after intravascular intervention. In particular, the present invention provides luminal prostheses which allow for programmed and controlled methylprednisolone delivery with increased efficiency and/or efficacy to selected locations within a patient's vasculature to inhibit restenosis. Moreover, the present invention provides minimal to no hindrance to endothelialization of the vessel wall.

The term "intravascular intervention" includes a variety of corrective procedures that may be performed to at least partially resolve a stenotic, restenotic, or thrombotic condition in a blood vessel, usually an artery, such as a coronary artery. Usually, the corrective procedure will comprise balloon angioplasty. The corrective procedure could also comprise directional atherectomy, rotational atherectomy, laser angioplasty, stenting, or the like, where the lumen of the treated blood vessel is enlarged to at least partially alleviate a stenotic condition which existed prior to the treatment.

Methylprednisolone acts by inhibiting inosine monophosphate dehydrogenase and guanosine monophosphate synthetase enzymes in the de novo purine biosynthetic pathway. This may cause the cells to accumulate in the G1-S phase of the cell cycle and thus result in inhibition of DNA synthesis and cell proliferation (hyperplasia). In the present application, the term "methylprednisolone" is used to refer to methylprednisolone itself and to pro-drugs and/or pharmaceutically derivatives thereof (precursor substances that are converted into an active form of methylprednisolone in the body).

In a first aspect of the present invention, a vascular prosthesis comprises an expansible structure which is implantable within a structure lumen and means on or within the structure for releasing methylprednisolone into the body lumen to minimize and/or inhibit smooth muscle cell proliferation. Methylprednisolone release will typically be at rates in a range from 5 µg/day to 200 µg/day, preferably in a range from 10 µg/day to 60 µg/day. The total amount of methylprednisolone released will typically be in a range from 100 µg to 10 mg, preferably in a range from 300 µg to 2 mg, more preferably in a range from 500 µg to 1.5 mg. Thus, the present invention also improves the efficiency and efficacy of methylprednisolone delivery by releasing methylprednisolone at a rate and/or time which inhibits smooth muscle cell proliferation.

The expansible structure may be in the form of a stent, which additionally maintains luminal patency, or may be in the form of a graft, which additionally protects or enhances the strength of a luminal wall. The expansible structure may be radially expansible and/or self-expanding and is preferably suitable for luminal placement in a body lumen. The body lumen may be any blood vessel in the patient's vasculature, including veins, arteries, aorta, and particularly including coronary and peripheral arteries, as well as previously implanted grafts, shunts, fistulas, and the like. It will be appreciated that the present invention may also be applied to other body lumens, such as the biliary duct, which are subject to excessive neoplastic cell growth, as well as to many internal corporeal tissue organs, such as organs, nerves, glands, ducts, and the like. An exemplary stent for use in the present invention is described in co-pending application Ser. No. 09/565,560, the full disclosure of which is incorporated herein by reference.

In a first embodiment, the means for releasing methylprednisolone comprises a matrix formed over at least a portion of the structure. The matrix may be composed of a material which is degradable, partially degradable, nondegradable polymer, synthetic, or natural material. Methylprednisolone may be disposed within the matrix or adjacent to the matrix in a pattern that provides the desired release rate. Alternatively, methylprednisolone may be disposed on or within the expansible structure adjacent to the matrix to provide the desired release rate. Suitable biodegradable or bioerodible matrix materials include polyanhydrides, polyorthoesters, polycaprolactone, poly vinly acetate, polyhydroxybutyrate-polyhyroxyvalerate, polyglycolic acid, polyactic/polyglycolic acid copolymers and other aliphatic polyesters, among a wide variety of polymeric substrates employed for this purpose. A preferred biodegradable matrix material of the present invention is a copolymer of poly-l-lactic acid and poly-e-caprolactone. Suitable nondegradable matrix materials include polyurethane, polyethylene imine, cellulose acetate butyrate, ethylene vinyl alcohol copolymer, or the like.

The polymer matrix may degrade by bulk degradation, in which the matrix degrades throughout, or preferably by surface degradation, in which a surface of the matrix degrades over time while maintaining bulk integrity. Hydrophobic matrices are preferred as they tend to release methylprednisolone at the desired release rate. Alternatively, a nondegradable matrix may release the substance by diffusion.

In some instances, the matrix may comprise multiple adjacent layers of same or different matrix material, wherein at least one layer contains methylprednisolone and another layer contains methylprednisolone, at least one substance other than methylprednisolone, or no substance. For example, methylprednisolone disposed within a top degradable layer of the matrix is released as the top matrix layer degrades and a second substance disposed within an adjacent nondegradable matrix layer is released primarily by diffusion. In some instances, multiple substances may be disposed within a single matrix layer.

The at least one substance other than methylprednisolone may comprise an immunosuppressive agent selected from the group consisting of rapamycin, mycophenolic acid, riboflavin, tiazofurin, mizoribine, FK 506, zafurin, and methotrexate. Such immunosuppressive substances, like methylprednisolone, may be useful in the present invention to inhibit smooth muscle cell proliferation. Alternatively, the at least one substance other than methylprednisolone may comprise at least one agent selected from the group consisting of anti-platelet agent (e.g., plavax, ticlid), anti-thrombotic agent (e.g., heparin, heparin derivatives), and IIb/IIa agent (e.g., integrilin, reopro). The agent may also be a prodrug of any of the above listed agents.

Additionally, a rate limiting barrier may be formed adjacent to the structure and/or the matrix. Such rate limiting barriers may be nonerodible or nondegradable, such as silicone, polytetrafluorethylene (PTFE), paralene, and parylast, and control the flow rate of release passing through the rate limiting barrier. In such a case, methylprednisolone may be released by diffusion through the rate limiting barrier. Furthermore, a biocompatible or blood compatible layer, such as polyethylene glycol (PEG), may be formed over the matrix or rate limiting barrier to make the delivery prosthesis more biocompatible.

In another embodiment, the means for releasing the substance may comprise a rate limiting barrier formed over at least a portion of the structure. Methylprednisolone may be disposed within the barrier or adjacent to the barrier. The rate limiting barrier may have a sufficient thickness so as to provide the desired release rate of methylprednisolone. Rate limiting barriers will typically have a total thickness in a range from 0.01 micron to 100 microns, preferably in a range from 0.1 micron to 10 microns, to provide methylprednisolone release at the desired release rate. The rate limiting barrier is typically nonerodible such as silicone, PTFE, parylast, polyurethane, parylene, or a combination thereof and methylprednisolone release through such rate limiting barriers is usually accomplished by diffusion. In some instances, the rate limiting barrier may comprise multiple adjacent layers of same or different barrier material, wherein at least one layer contains methylprednisolone and another layer contains methylprednisolone, at least one substance other than methylprednisolone, or no substance. Multiple substances may also be contained within a single barrier layer.

In yet another embodiment, the means for releasing the substance comprises a reservoir on or within the structure containing methylprednisolone and a cover over the reservoir. The cover may be degradable or partially degradable over a preselected time period so as to provide the desired methylprednisolone release rate. The cover may comprise a polymer matrix, as described above, which contains methylprednisolone within the reservoir. A rate limiting barrier, such as silicone, may additionally be formed adjacent to the reservoir and/or the cover, thus allowing methylprednisolone to be released by diffusion through the rate limiting barrier. Alternatively, the cover may be a nondegradable matrix or a rate limiting barrier.

Another vascular prosthesis comprises an expansible structure which is implantable within a body lumen and a rate limiting barrier on the structure for releasing methylprednisolone into the body lumen to inhibit smooth muscle cell proliferation. The barrier comprises multiple layers, wherein each layer comprises parylast or paralene and has a thickness in a range from 50 nm to 10 microns. At least one layer contains methylprednisolone and another layer contains methylprednisolone, at least one substance other than methylprednisolone, or no substance.

Yet another vascular prosthesis comprises an expansible structure, a source of methylprednisolone on or within the structure, and a source of at least one other substance in addition to methylprednisolone on or within the structure. The methylprednisolone is released from the source when the expansible structure is implanted in a blood vessel. The at least one additional substance is released from the source when the expansible structure is implanted in a blood vessel. Each source may comprise a matrix, rate limiting membrane, reservoir, or other rate controlling means as described herein. The at least one additional substance may be an immunosuppressive substance selected from the group consisting of rapamycin, mycophenolic acid, riboflavin, tiazofurin, mizoribine, FK 506, zafurin, and methotrexate. Optionally, the at least one additional substance may comprise at least one agent selected from the group consisting of anti-platelet agent, anti-thrombotic agent, and IIb/IIa agent.

In another aspect of the present invention, methods for inhibiting restenosis in a blood vessel following recanalization of the blood vessel are provided. For example, one method may include implanting a vascular prosthesis in a blood vessel to prevent reclosure of the blood vessel. Methylprednisolone is then released into the blood vessel so as to inhibit smooth muscle cell proliferation. The releasing comprises delaying substantial release of methylprednisolone for at least one hour following implantation of the prosthesis. The inhibiting release may comprise slowing release from a reservoir with a material that at least partially degrades in a vascular environment over said one hour. In some instances, release may be slowed with a matrix that at least partially degrades in a vascular environment over said one hour. In other instances, release may be slowed with a nondegradable matrix or rate limiting barrier that allows diffusion of methylprednisolone through said nondegradable matrix or barrier after said one hour. Methylprednisolone release will typically be at rates in a range from 5 µg/day to 200 µg/day, preferably in a range from 10 µg/day to 60 µg/day. Typically, methylprednisolone is released within a time period of 1 day to 45 days in a vascular environment, preferably in a time period of 7 day to 21 days in a vascular environment.

The prosthesis may be coated with a matrix or barrier by spraying, dipping, deposition, or painting. Such coatings may be non-uniform. For example, the coating may be applied to only one side of the prosthesis or the coating may be thicker on one side. Likewise, the prosthesis may also incorporate methylprednisolone by coating, spraying, dipping, deposition, chemical bonding, or painting methylprednisolone on all or partial surfaces of the prosthesis.

Another method for inhibiting restenosis in a blood vessel following recanalization of the blood vessel comprises implanting a vascular prosthesis in the blood vessel to prevent reclosure. Methylprednisolone and at least one other substance in addition to methylprednisolone are released when the prosthesis is implanted in the blood vessel. The at least one additional substance may be an immunosuppressive substance selected from the group consisting of rapamycin, mycophenolic acid, riboflavin, tiazofurin, mizoribine, FK 506, zafurin, and methotrexate. Preferably, the immunosuppressive substance is mycophenolic acid or mizoribine. Typically, methylprednisolone may be released within a time period of 2 days to 3 months. Optionally, the at least one additional substance may comprise at least one agent selected from the group consisting of anti-platelet agent, antithrombotic agent, and IIb/IIIa agent. Release of methylprednisolone and the at least additional substance may be simultaneous or sequential.

DESCRIPTION OF THE SPECIFIC EMBODIMENTS

The present invention provides improved devices and methods for inhibiting restenosis and hyperplasia after intravascular intervention. In particular, the present invention provides luminal prostheses which allow for programmed and controlled methylprednisolone delivery with increased efficacy to selected locations within a patient's vasculature to inhibit restenosis.

Figure 1:
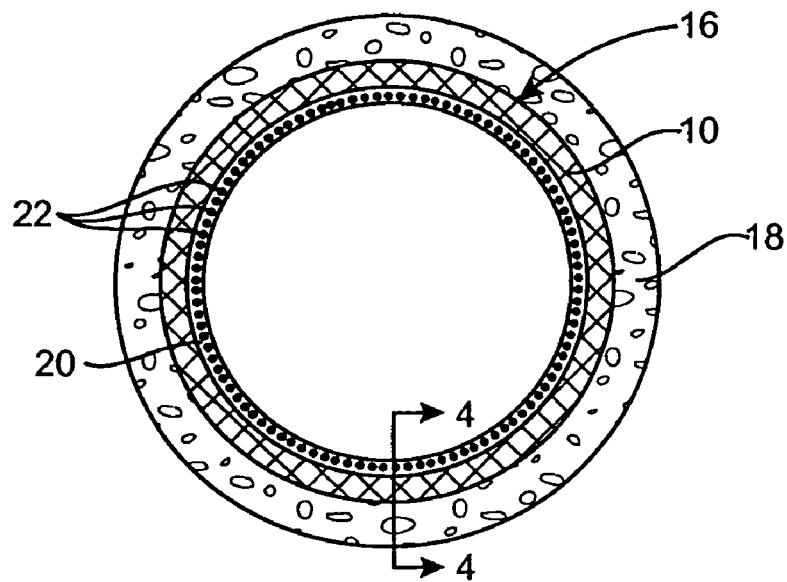
FIGS. 1 and 1A are cross-sectional views of a delivery prosthesis implanted in a body lumen.
Figure 1A:
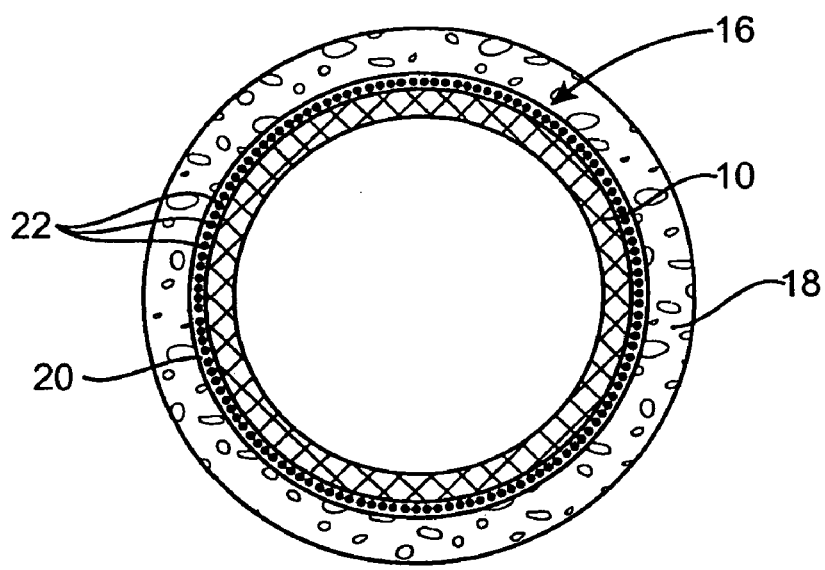

FIGS. 1 and 1A illustrate a delivery prosthesis 16 constructed in accordance with the principles of the present invention. The luminal delivery prosthesis 16 comprises a scaffold 10 which is implantable in a body lumen 18 and means 20 on the scaffold 10 for releasing methylprednisolone 22. Methylprednisolone 22 is released over a predetermined time pattern comprising an initial phase wherein methylprednisolone delivery rate is below a threshold level and a subsequent phase wherein methylprednisolone delivery rate is above a threshold level.

It will be appreciated that the following depictions are for illustration purposes only and does not necessarily reflect the actual shape, size, or distribution of the delivery prosthesis 16. For example, the means or source 20 for releasing methylprednisolone (matrix, rate limiting barrier, reservoir, and other rate controlling means) may be coupled to a portion, inside, outside, or both sides of the prosthesis. The term "coupled to" includes connected to, attached to, adjacent to, and like configurations. Additionally, methylprednisolone 22 may be disposed within the means or source for releasing the methylprednisolone, on or within the scaffold, or the methylprednisolone may alternatively be adhering to the scaffold, bonded to the scaffold, or entrapped within the scaffold. This applies to all depictions hereinafter.

The body lumen 18 may be any blood vessel in the patient's vasculature, including veins, arteries, aorta, and particularly including coronary and peripheral arteries, as well as previously implanted grafts, shunts, fistulas, and the like. It will be appreciated that the present invention may also find use in body lumens 18 other than blood vessels. For example, the present invention may be applied to many internal corporeal tissue organs, such as organs, nerves, glands, ducts, and the like.

The scaffold 10 will comprise a stent or graft, which may be partially or completely covered by one or more layer of cells. As a stent example, the scaffold 10 will usually comprise at least two radially expansible, usually cylindrical, ring segments. Typically, the scaffold 10 will have at least four, and often five, six, seven, eight, ten, or more ring segments. At least some of the ring segments will be adjacent to each other but others may be separated by other non-ring structures.

By "radially expansible," it is meant that the segment can be converted from a small diameter configuration to a radially expanded, usually cylindrical, configuration which is achieved when the scaffold 10 is implanted at a desired target site. The scaffold 10 may be minimally resilient, e.g., malleable, thus requiring the application of an internal force to expand and set it at the target site. Typically, the expansive force can be provided by a balloon, such as the balloon of an angioplasty catheter for vascular procedures. The scaffold 10 preferably provides sigmoidal links between successive unit segments which are particularly useful to enhance flexibility and crimpability of the stent.

Alternatively, the scaffold 10 can be self-expanding. Such self-expanding structures are provided by utilizing a resilient material, such as a tempered stainless steel or a superelastic alloy such as a Nitinol™ alloy, and forming the body segment so that it possesses its desired, radially-expanded diameter when it is unconstrained, i.e. released from the radially constraining forces of a sheath. In order to remain anchored in the body lumen, the scaffold 10 will remain partially constrained by the lumen. The self-expanding scaffold 10 can be tracked and delivered in its radially constrained configuration, e.g., by placing the scaffold 10 within a delivery sheath or tube and removing the sheath at the target site.

The dimensions of the scaffold 10 will depend on its intended use. Typically, the scaffold 10 will have a length in a range from about 5 mm to 100 mm, usually being from about 8 mm to 50 mm, for vascular applications. The small (radially collapsed) diameter of cylindrical scaffold 10 will usually be in a range from about 0.5 mm to 10 mm, more usually being in a range from 0.8 mm to 8 mm for vascular applications. The expanded diameter will usually be in a range from about 1.0 mm to 100 mm, preferably being in a range from about 2.0 mm to 30 mm for vascular applications. The scaffold 10 will have a thickness in a range from 0.025 mm to 2.0 mm, preferably being in a range from 0.05 mm to 0.5 mm.

The ring segments may be formed from conventional materials used for body lumen stents and grafts, typically being formed from malleable metals, such as 300 series stainless steel, or from resilient metals, such as superelastic and shape memory alloys, e.g., Nitinol™ alloys, spring stainless steels, and the like. It is possible that the body segments could be formed from combinations of these metals, or combinations of these types of metals and other non-metallic materials. Additional structures for the body or unit segments of the present invention are illustrated in U.S. Pat. Nos. 5,195,417; 5,102,417; and 4,776,337, the full disclosures of which are incorporated herein by reference.

Figure 2:
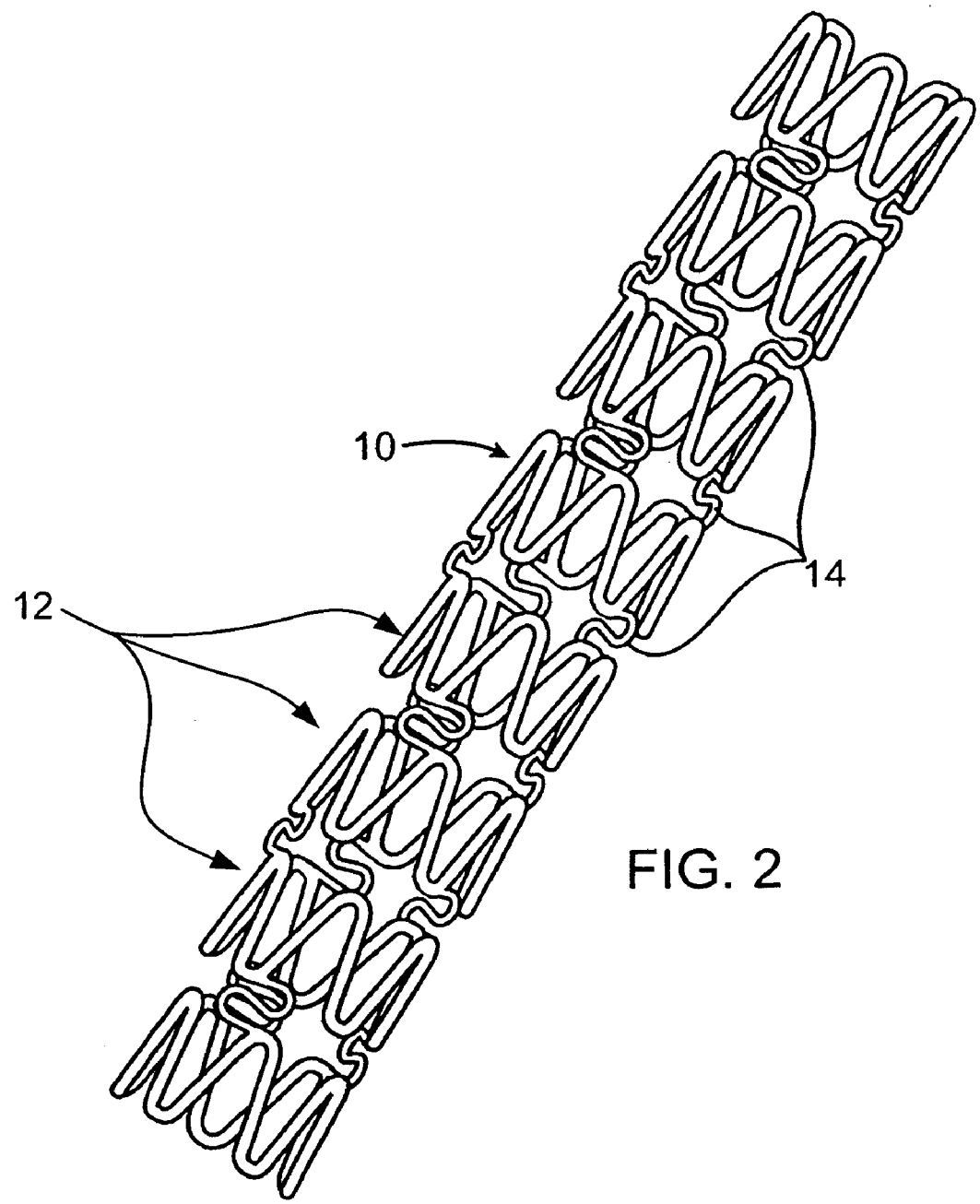
FIG. 2 is a digital photograph of an exemplary stent of the delivery prosthesis prior to expansion.

Referring now to FIG. 2, an exemplary stent 10 (which is described in more detail in co-pending application Ser. No. 09/565,560) for use in the present invention comprises from 4 to 50 ring segments 12 (with seven being illustrated). Each ring segment 12 is joined to the adjacent ring segment by at least one of sigmoidal links 14 (with three being illustrated). Each ring segment 12 includes a plurality, e.g., six strut/hinge units, and two out of each six hinge/strut structures on each ring segment 12 will be joined by the sigmoidal links 14 to the adjacent ring segment. FIG. 2 shows the stent 10 in a collapsed or narrow diameter configuration.

Figure 3:
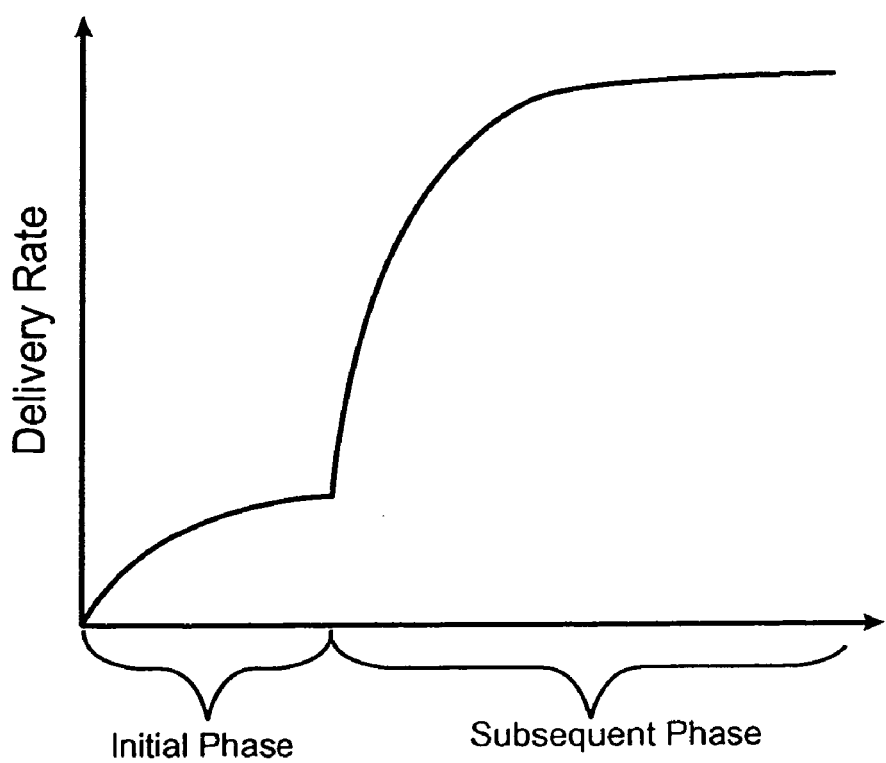
FIG. 3 is a graphical representation of substance release over a predetermined time period.

Referring now to FIG. 3, a graphical representation of methylprednisolone release over a predetermined time period is illustrated. The predetermined time pattern of the present invention improves the efficiency of drug delivery by releasing methylprednisolone at a lower or minimal delivery rate during an initial phase. Once a subsequent phase is reached, the delivery rate of methylprednisolone may be substantially higher. Thus, time delayed methylprednisolone release can be programmed to impact restenosis at the onset of initial cellular deposition or proliferation (hyperplasia). The present invention can further minimize methylprednisolone washout by timing methylprednisolone release to occur after at least initial cellularization. Moreover, the predetermined time pattern may reduce methylprednisolone loading and/or methylprednisolone concentration as well as potentially provide minimal to no hindrance to endothelialization of the vessel wall due to the minimization of drug washout and the increased efficiency of methylprednisolone release.

Methylprednisolone is an antiproliferative antimetabolite which inhibits inosine monophosphate dehydrogenase and guanosine monophosphate synthetase enzymes in the de novo purine biosynthesis pathway. This may cause the cells to accumulate in the G1-S phase of the cell cycle and thus result in inhibition of DNA synthesis and cell proliferation (hyperplasia). Another way to administer methylprednisolone is through the use of a prodrug (precursor substances that are converted into an active form in the body). In addition to methylprednisolone, a number of drugs which inhibit inosine monophosphate dehydrogenase may be useful in the present invention to inhibit smooth muscle cell proliferation. Examples of such drugs include rapamycin, mycophenolic acid, riboflavin, tiazofurin, mizoribine, FK 506, zafurin, and methotrexate.

Methylprednisolone delivery may perform a variety of functions, including preventing or minimizing proliferative/ restenotic activity, inhibiting thrombus formation, inhibiting platelet activation, preventing vasospasm, or the like. The total amount of methylprednisolone released depends in part on the level and amount of vessel injury, and will typically be in a range from 100 µg to 10 mg, preferably in a range from 300 µg to 2 mg, more preferably in a range from 500 µg to 1.5 mg. The release rate during the initial phase will typically be from 0 µg/day to 50 µg/day, usually from 5 µg/day to 30 µg/day. The methylprednisolone release rate during the subsequent phase will be much higher, typically being in the range from 5 µg/day to 200 µg/day, usually from 10 µg/day to 100 µg/day. Thus, the initial release rate will typically be from 0% to 99% of the subsequent release rates, usually from 0% to 90%, preferably from 0% to 75%. A mammalian tissue concentration of the substance at an initial phase will typically be within a range from 0 µg/mg of tissue to 100 µg/mg of tissue, preferably from 0 µg/mg of tissue to 10 µg/mg of tissue. A mammalian tissue concentration of the substance at a subsequent phase will typically be within a range from 1 picogram/mg of tissue to 100 µg/mg of tissue, preferably from 1 nanogram/mg of tissue to 10 µg/mg of tissue.

The duration of the initial, subsequent, and any other additional phases may vary. Typically, the initial phase will be sufficiently long to allow initial cellularization or endothelialization of at least part of the stent, usually being less than 12 weeks, more usually from 1 hour to 8 weeks, more preferably from 12 hours to 2 weeks, most preferably from 1 day to 1 week. The durations of the subsequent phases may also vary, typically being from 4 hours to 24 weeks, more usually from 1 day to 12 weeks, more preferably in a time period of 2 days to 8 weeks in a vascular environment, most preferably in a time period of 3 days to 50 days in a vascular environment.

In some instances, the release profile of methylprednisolone over a predetermined time may allow for a higher release rate during an initial phase, typically from 40 µg/day to 300 µg/day, usually from 40 µg/day to 200 µg/day. In such instances, methylprednisolone release during the subsequent phase will be much lower, typically being in the range from 1 µg/day to 100 µg/day, usually from 10 µg/day to 40 µg/day. The duration of the initial phase period for the higher release rate will be in a range from 1 day to 7 days, with the subsequent phase period for the lower release rate being in a range from 2 days to 45 days. A mammalian tissue concentration of the substance at the initial phase of 1–7 days will typically be within a range from 10 nanogram/mg of tissue to 100 µg/mg of tissue. A mammalian tissue concentration of the substance at the subsequent phase of 2–45 days will typically be within a range from 0.1 nanogram/mg of tissue to 10 µg/mg of tissue. In other instances, the release of methylprednisolone may be constant at a rate between 5 µg/day to 200 µg/day for a duration of time in the range from 1 day to 45 days. A mammalian tissue concentration over this period of 1–45 days will typically be within a range from 1 nanogram/mg of tissue to 10 µg/mg of tissue.

Figure 4:
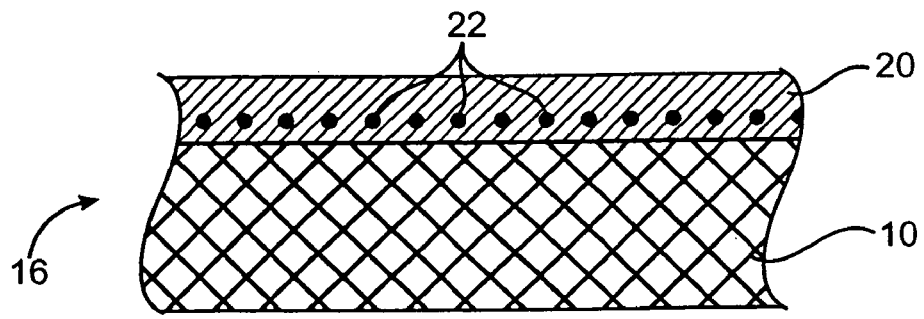
FIG. 4 is a partial cross-sectional view of a delivery prosthesis having a matrix for releasing a substance disposed within the matrix.

In one embodiment, the means for releasing methylprednisolone comprises a matrix or coat 20 formed over at least a portion of the scaffold 10, wherein the matrix 20 is composed of material which undergoes degradation. As shown in FIG. 4, methylprednisolone 22 may be disposed within the matrix 20 in a pattern that provides the desired release rates. Alternatively, methylprednisolone 22 may be disposed within or on the scaffold 10 under the matrix 20 to provide the desired release rates, as illustrated respectively in FIGS. 5 and 6.

It will be appreciated that the scaffold 10 acts as a mechanical support for the delivery matrix 20, thus allowing a wide variety of materials to be utilized as the delivery matrix 20. Suitable biodegradable or bioerodible matrix materials include polyanhydrides, polyorthoesters, polycaprolactone, poly vinly acetate, polyhydroxybutyrate-polyhyroxyvalerate, polyglycolic acid, polyactic/polyglycolic acid copolymers and other aliphatic polyesters, among a wide variety of synthetic or natural polymeric substrates employed for this purpose.

An example of a biodegradable matrix material of the present invention is a copolymer of poly-l-lactic acid (having an average molecular weight of about 200,000 daltons) and poly-e-caprolactone (having an average molecular weight of about 30,000 daltons). Poly-e-caprolactone (PCL) is a semi crystalline polymer with a melting point in a range from 59° C. to 64° C. and a degradation time of about two years. Thus, poly-l-lactic acid (PLLA) can be combined with PCL to form a matrix that generates the desired release rates. A preferred ratio of PLLA to PCL is 75:25 (PLLA/PCL). As generally described by Rajasubramanian et al. in *ASAIO Journal*, 40, pp. M584–589 (1994), the full disclosure of which is incorporated herein by reference, a 75:25 PLLA/ PCL copolymer blend exhibits sufficient strength and tensile properties to allow for easier coating of the PLLA/PLA matrix on the scaffold. Additionally, a 75:25 PLLA/PCL copolymer matrix allows for controlled drug delivery over a predetermined time period as a lower PCL content makes the copolymer blend less hydrophobic while a higher PLLA content leads to reduced bulk porosity.

The polymer matrix 20 may degrade by bulk degradation, in which the matrix degrades throughout, or preferably by surface degradation, in which only a surface of the matrix degrades over time while maintaining bulk integrity. Alternatively, the matrix 20 may be composed of a nondegradable material which releases methylprednisolone by diffusion. Suitable nondegradable matrix materials include polyurethane, polyethylene imine, cellulose acetate butyrate, ethylene vinyl alcohol copolymer, or the like.

Figure 7:
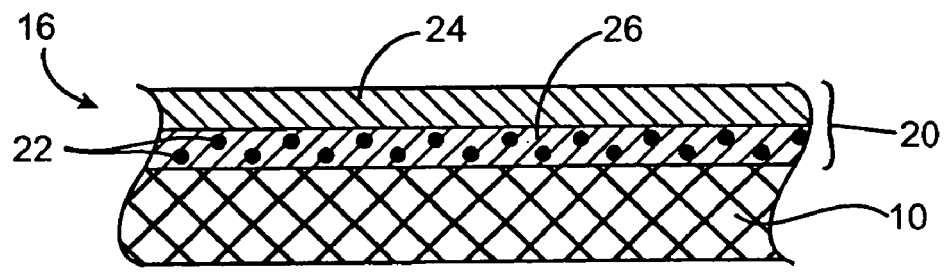
FIG. 7 is a partial cross-sectional view of a delivery prosthesis having multiple matrix layers.
Figure 8:
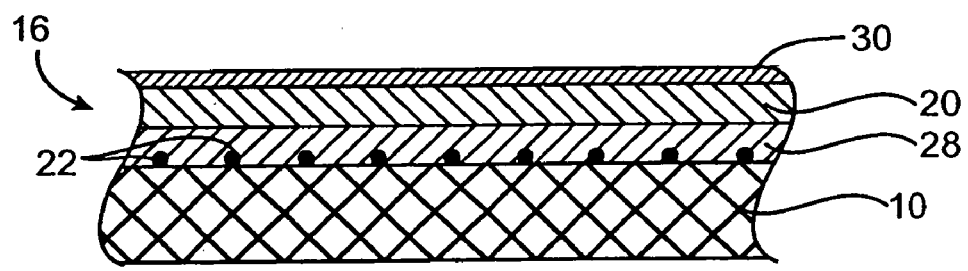
FIG. 8 is a partial cross-sectional view of a delivery prosthesis having a matrix between a rate limiting barrier and a biocompatible layer.

Referring now to FIG. 7, the matrix 20 may comprise multiple layers 24 and 26, each layer containing methylprednisolone, a different substance, or no substance. As shown, a top layer 24 may contain no substance while a bottom layer 26 contains methylprednisolone 22. As the top layer 24 degrades, the methylprednisolone 22 delivery rate increases. Additionally, the present invention may employ a rate limiting barrier 28 formed between the scaffold 10 and the matrix 20, as illustrated in FIG. 8, or may optionally be formed over the matrix 20. Such rate limiting barriers 28 may be nonerodible and control the flow rate of release by diffusion of the methylprednisolone 22 through the barrier 28. Suitable nonerodible rate limiting barriers 28 include silicone, PTFE, parylast, and the like. Furthermore, a layer 30, such as polyethylene glycol (PEG), and the like, may be formed over the matrix 20 to make the delivery prosthesis 16 more biocompatible.

Figure 9:
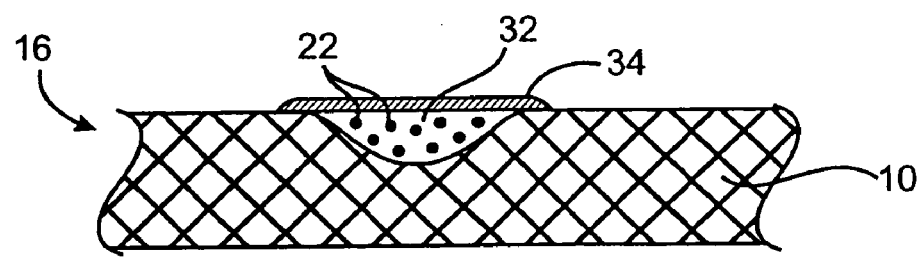
FIG. 9 is a partial cross-sectional view of a delivery prosthesis having a reservoir type releasing means.

In another embodiment, as illustrated in FIG. 9, the means for releasing methylprednisolone comprises a reservoir 32 on or within the scaffold 10 containing the methylprednisolone 22 and a cover 34 over the reservoir 32. The cover 34 is degradable over a preselected time period so that release of methylprednisolone 22 from the reservoir 32 begins substantially after the preselected time period. The cover 34, in this example, may comprise a polymer matrix, as described above, which contains the methylprednisolone 22 within the reservoir 32 so that the matrix 34 is replenished by the methylprednisolone 22 within the reservoir 32. A rate limiting barrier 28, as described with reference to FIG. 8, may additionally be formed between the reservoir 32 and the cover 34, or on top of the cover 34, thus allowing the methylprednisolone to be released by diffusion through the rate limiting barrier 28.

In operation, methods for methylprednisolone delivery comprise providing a luminal prosthesis incorporating or coupled to the methylprednisolone. The prosthesis is coated with a matrix which undergoes degradation in a vascular environment (FIGS. 4–9). The prosthesis is implanted in a body lumen (FIGS. 12A–12C) so that at least a portion of the matrix degrades over a predetermined time period and substantial methylprednisolone release begins after the portion has degraded. Optionally, the prosthesis may be coated with a rate limiting barrier or nondegradable matrix having a sufficient thickness to allow diffusion of the methylprednisolone through the barrier or nondegradable matrix. The prosthesis is implanted in a body lumen so that substantial methylprednisolone release from the barrier or nondegradable matrix begins after a preselected time period. As the proliferative effects of restenosis usually occur within a few weeks to a few months, substantial release of methylprednisolone will begin within a time period of 4 hours to 24 weeks in a vascular environment, preferably in a time period of 1 day to 12 weeks in a vascular environment, more preferably in a time period of 2 days to 8 weeks in a vascular environment, most preferably in a time period of 3 days to 50 days in a vascular environment.

Figure 5:
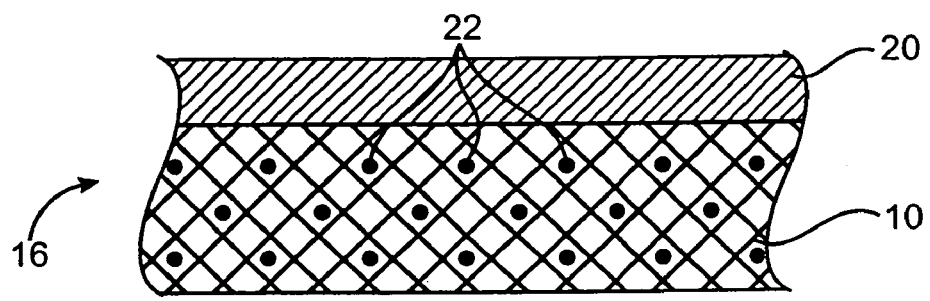
FIG. 5 is a partial cross-sectional view of a delivery prosthesis having a scaffold containing a substance.
Figure 6:
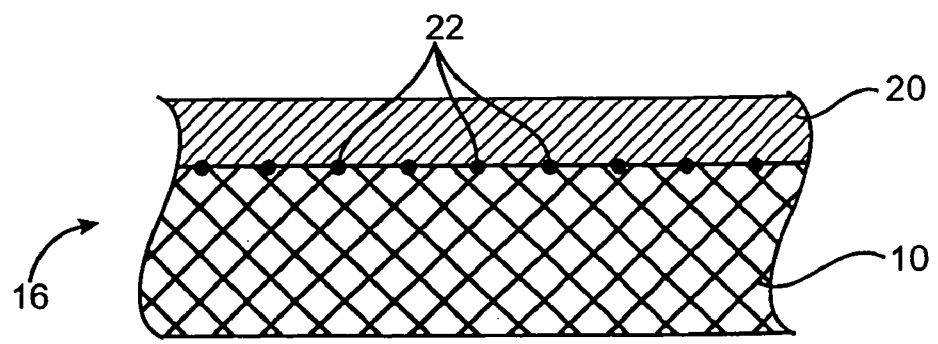
FIG. 6 is a partial cross-sectional view of a delivery prosthesis having a scaffold and a substance disposed on a scaffold surface.

Methylprednisolone may be incorporated in a reservoir in a scaffold, as shown in FIG. 9, or on a scaffold. In this configuration, the reservoir is covered by the matrix so that methylprednisolone release begins substantially after the matrix has degraded sufficiently to uncover the reservoir. Alternatively, methylprednisolone may be disposed in the matrix with the matrix coating a scaffold (FIG. 7). In this configuration, an outer layer of the matrix is substantially free from methylprednisolone so that methylprednisolone release will not substantially begin until the outer layer has degraded. Optionally, methylprednisolone may be disposed within or on a scaffold coated by the matrix (FIGS. 5–6).

The prosthesis 16 may incorporate methylprednisolone 22 by coating, spraying, dipping, deposition, or painting the methylprednisolone on the prosthesis. Usually, the methylprednisolone 22 is dissolved in a solvent to make a solution. Suitable solvents include aqueous solvents (e.g., water with pH buffers, pH adjusters, organic salts, and inorganic salts), alcohols (e.g., methanol, ethanol, propanol, isopropanol, hexanol, and glycols), nitriles (e.g., acetonitrile, benzonitrile, and butyronitrile), amides (e.g., formamide and N dimethylformamide), ketones, esters, ethers, DMSO, gases (e.g., $CO_2$), and the like. For example, the prosthesis may be sprayed with or dipped in the solution and dried so that methylprednisolone crystals are left on a surface of the prosthesis. Alternatively, the prosthesis 16 may be coated with the matrix solution by spraying, dipping, deposition, or painting the polymer solution onto the prosthesis. Usually, the polymer is finely sprayed on the prosthesis while the prosthesis is rotating on a mandrel. A thickness of the matrix coating may be controlled by a time period of spraying and a speed of rotation of the mandrel. The thickness of the matrix coating is typically in a range from 0.01 micron to 100 microns, preferably in a range from 0.1 micron to 10 microns. Once the prosthesis has been coated with the methylprednisolone/matrix, the stent may be placed in a vacuum or oven to complete evaporation of the solvent.

For example, a stainless steel Duraflex™ stent, having dimensions of 3.0 mm×14 mm is sprayed with a solution of 25 mg/ml methylprednisolone (sold commercially by SIGMA CHEMICALS) in a 100% ethanol or methanol solvent. The stent is dried and the ethanol is evaporated leaving the methylprednisolone on a stent surface. A 75:25 PLLA/PCL copolymer (sold commercially by POLYSCIENCES) is prepared in 1,4 Dioxane (sold commercially by ALDRICH CHEMICALS). The methylprednisolone loaded stent is loaded on a mandrel rotating at 200 rpm and a spray gun (sold commercially by BINKS MANUFACTURING) dispenses the copolymer solution in a fine spray on to the methylprednisolone loaded stent as it rotates for a 10–30 second period. The stent is then placed in a oven at 25–35° C. up to 24 hours to complete evaporation of the solvent.

In a further embodiment, the means for releasing methylprednisolone may comprise a reservoir on or within the scaffold holding the methylprednisolone (as shown in FIG. 9) and an external energy source for directing energy at the prosthesis after implantation to effect release of the methylprednisolone. A matrix may be formed over the reservoir to contain the methylprednisolone within the reservoir. Alternatively, the means for releasing methylprednisolone may comprise a matrix formed over at least a portion of the scaffold (as shown in FIGS. 4–6), wherein the methylprednisolone is disposed under or within the matrix, and an external energy source for directing energy at the prosthesis after implantation to effect release of the methylprednisolone. Suitable external energy source include ultrasound, magnetic resonance imaging, magnetic field, radio frequency, temperature change, electromagnetic, x-ray, radiation, heat, gamma, and microwave.

For example, an ultrasound external energy source may be used having a frequency in a range from 20 kHz to 100 MHz, preferably in a range from 0.1 MHz to 20 MHz, and an intensity level in a range from 0.05 W/cm$^2$ to 10 W/cm$^2$, preferably in a range from 0.5 W/cm$^2$ to 5 W/cm$^2$. The ultrasound energy should be directed at the prosthesis 16 from a distance in a range from 1 mm to 30 cm, preferably in a range from 1 cm to 20 cm. The ultrasound may be continuously applied or pulsed, for a time period in a range from 5 sec to 30 minutes, preferably in a range from 1 minute to 15 minutes. The temperature of the delivery prosthesis 16 during this period will be in a range from 37° C. to 48° C. The ultrasound may be used to increase a porosity of the prosthesis 16, thereby allowing release of the methylprednisolone 22 from the prosthesis 16.

Figure 10:
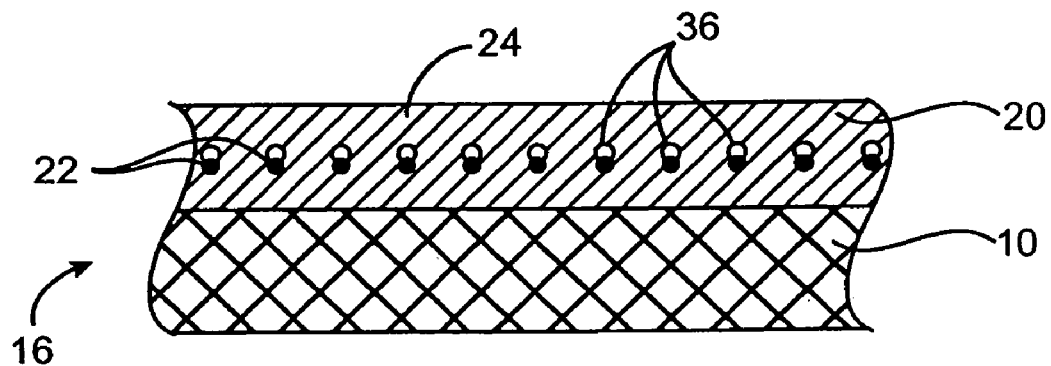
FIG. 10 is a partial cross-sectional view of a delivery prosthesis having magnetic releasing means.

In yet another embodiment, as depicted in FIG. 10, means for releasing methylprednisolone comprises magnetic particles 36 coupled to the methylprednisolone 22 and a magnetic source for directing a magnetic field at the prosthesis 16 after implantation to effect release of the methylprednisolone 22. Optionally, the means for releasing methylprednisolone may comprise magnetic particles 26 coupled to a matrix 20 formed over the scaffold 10 and a magnetic source for directing a magnetic field at the prosthesis 16 after implantation to effect release of the methylprednisolone 22. Methylprednisolone 22 may be disposed under (FIGS. 5 and 6) or within the matrix 20 (FIG. 10). The magnetic particles 36 may be formed from magnetic beads and will typically have a size in a range from 1 nm to 100 nm. The magnetic source exposes the prosthesis 16 to its magnetic field at an intensity typically in the range from 0.01T to 2T, which will activate the magnetic particles 36, and thereby effect release of the methylprednisolone from the prosthesis.

Figure 11:
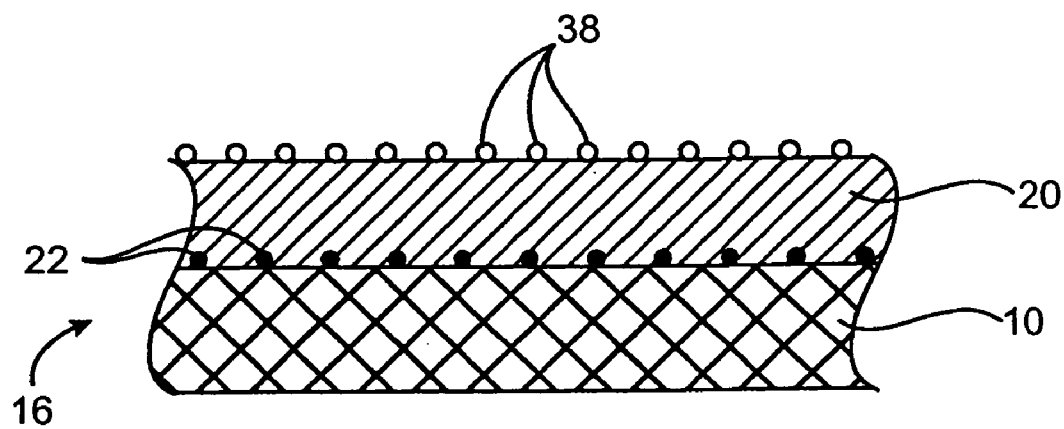
FIG. 11 is a partial cross-sectional view of a delivery prosthesis with cellular growth.

Referring now to FIG. 11, improved methods for delivering a pharmacological agent to an artery are illustrated. The method is of the type where a prosthesis 16 is implanted in the artery 18 and the prosthesis 16 releases the pharmacological agent 22. The improvement comprises implanting a prosthesis 16 that is programmed to begin substantial release of the pharmacological agent 22 beginning after growth of at least one layer of cells 38 over a part of the prosthesis. The cells 38 will typically comprise inflammation, smooth muscle, or endothelial cells, indicating the onset of restenosis.

Figure 12A:
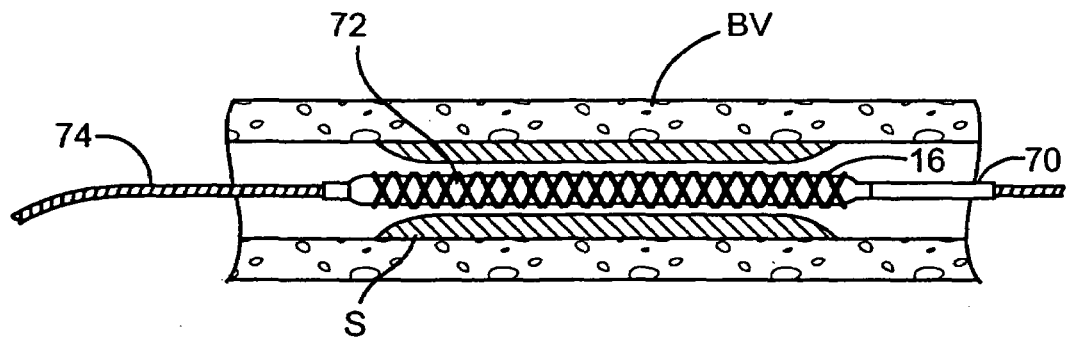
FIGS. 12A–12C illustrates a method for positioning a delivery prosthesis in a blood vessel in order to deliver a substance therein.
Figure 12B:
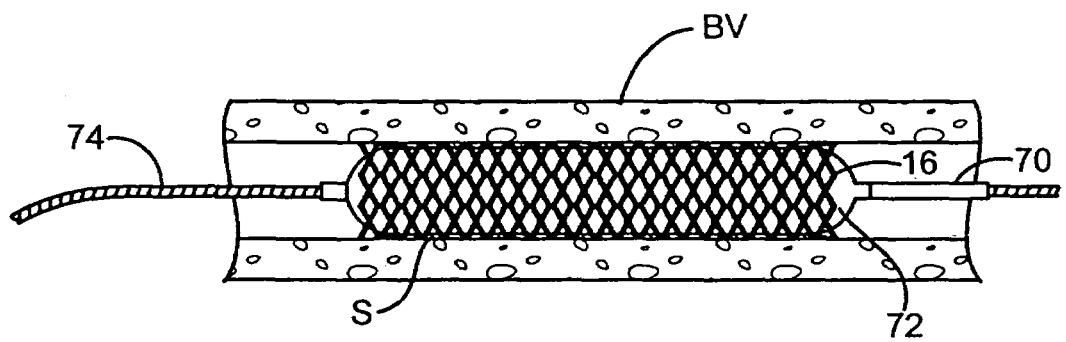
Figure 12C:
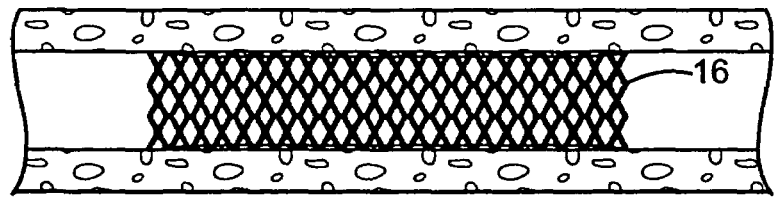

Referring now to FIGS. 12A–12C, a method for positioning the delivery prosthesis 16 in a body lumen in order to deliver methylprednisolone 22 therein will be described. As shown in FIG. 12A, a balloon dilation catheter 70 will typically be used to deliver the prosthesis 16 to a region of stenosis S in a blood vessel BV. The prosthesis 16 is initially carried in its radially collapsed diameter configuration on an deflated balloon 72 of the balloon catheter 70. The balloon catheter is typically introduced over a guidewire 74 under fluoroscopic guidance. The catheters and guidewires may be introduced through conventional access sites to the vascular system, such as through the femoral artery, or brachial, subclavian or radial arteries, for access to the coronary arteries. After the delivery prosthesis 16 is properly positioned within the region of stenosis (FIG. 12A), the balloon 72 will be inflated to radially expand the prosthesis 16 (FIG. 12B) within the stenotic region. The balloon 72 may then be deflated, and the catheter 70 may be withdrawn over the guidewire 74. After removal of the guidewire 74, the expanded prosthesis 16 will be left in place, as illustrated in FIG. 12C, to provide luminal methylprednisolone delivery as described above to inhibit restenotic effects.

In general, it will be possible to combine elements of the differing prostheses and treatment methods as described above. For example, a prosthesis having reservoir means for releasing methylprednisolone as illustrated in FIG. 9 may further incorporate a rate limiting barrier as illustrated in FIG. 8. Additionally, methods of the present invention may combine balloon angioplasty and/or other interventional treatments to resolve a stenotic site with the presently described luminal methylprednisolone delivery treatments.

The use of methylprednisolone for intravascular delivery is further illustrated by the following non-limiting examples.

EXAMPLE 1

Methylprednisolone Loaded on Vascular Stent

A stainless steel Duraflex™ stent, having dimensions of 3.0 mm×14 mm is sprayed with a solution of 25 mg/ml methylprednisolone (sold commercially by SIGMA CHEMICALS) in a 100% ethanol or methanol solvent. The stent is dried and the ethanol is evaporated leaving the methylprednisolone on a stent surface. A 75:25 PLLA/PCL copolymer (sold commercially by POLYSCIENCES) is prepared in 1,4 Dioxane (sold commercially by ALDRICH CHEMICALS). The methylprednisolone loaded stent is loaded on a mandrel rotating at 200 rpm and a spray gun (sold commercially by BINKS MANUFACTURING) dispenses the copolymer solution in a fine spray on to the methylprednisolone loaded stent as it rotates for a 10–30 second period. The stent is then placed in a oven at 25–35° C. up to 24 hours to complete evaporation of the solvent.

EXAMPLE 2

Increased Loading of Methylprednisolone on Vascular Stent

Stainless steel Duraflex stent (3.0×13 mm) is laser cut from a SS tube. The surface area for loading the drug is increased by increasing the surface roughness of the stent. The surface area and the volume of the stent can be further increased by creating 10 nm wide and 5 nm deep grooves along the links of the stent strut. The grooves are created in areas which experience low stress during expansion so that the stent radial strength is not compromised. The drug can then be loaded on the stent and in the groove by dipping or spraying the stent in methylprednisolone solution prepared in low surface tension solvent such as isopropyl alcohol, ethanol, or methanol. The stent is then dried and the drug resides on the stent surface and in the grooves, which serve as a drug reservoir. Paralene is then deposited on the stent to serve as a rate limiting barrier. The drug elutes from the stent over a period of time in the range from 1 day to 45 days.

EXAMPLE 3

The methylprednisolone substance is dissolved in methanol, then sprayed on the stent, and left to dry evaporating the solvent with the methylprednisolone remaining on the stent surface. A matrix or barrier (silicone, polytetrafluorethylene, parylast, parylene) is sprayed or deposited on the stent encapsulating the methylprednisolone. The amount of methylprednisolone varies from 100 micrograms to 2 milligrams, with release rates from I day to 45 days.

EXAMPLE 4

A matrix with methylprednisolone coated on a stent, as described in Example 2, and then coated or sprayed with a top coat of a rate limiting barrier (and/or a matrix without a drug so to act as a rate limiting barrier). Alternatively, methylprednisolone may be coated on a stent via a rate limiting barrier, and then covered with a top coat (another barrier or matrix). Use of top coats provide further control of release rate, improved biocompatibility, and/or resistance to scratching and cracking upon stent delivery or expansion.

EXAMPLE 5

Methylprednisolone may be combined with other drugs (cytotoxix drugs, cytostatic drugs, or psoriasis drugs, such as, mycophenolic acid, riboflavin, tiazofurin, mizoribine, FK 506, zafurin, methotrexate). For example, one drug is in or coupled a first coat while methylprednisolone is in or coupled to a second coat. Methylprednisolone may be released for a longer period than any one of the other above mentioned drugs since methylprednisolone has little impact on endothelialization in humans, which is needed for complete healing of a vessel.

EXAMPLE 6

A combination of multiple drugs that are individually included in different coats. The coats may release the multiple drugs simultaneously and/or sequentially. The drugs may be selected from a methylprednisolone class of inhibitors of de novo nucleotide synthesis or from classes of glucocorticosteroids, immunophilin-binding drugs, deoxyspergualin, FTY720, protein drugs, and peptides. This can also apply to any combination of drugs from the above classes that is coupled to a stent with the addition of other cytotoxic drugs.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A method for inhibiting restenosis in a blood vessel following recanalization of the blood vessel, said method comprising:
   implanting a vascular prosthesis in the blood vessel; and
   releasing methylprednisolone and mycophenolic acid from the prosthesis when implanted in the blood vessel.

2. A method as in claim 1, wherein methylprednisolone is released from the prosthesis at a rate between 5 µg/day to 200 µg/day.

3. A method as in claim 2, wherein methylprednisolone is released at a rate between 10 µg/day to 60 µg/day.

4. A method as in claim 1, wherein methylprednisolone is released from the prosthesis within a time period of 1 day to 45 days in a vascular environment.

5. A method as in claim 4, wherein methylprednisolone is released within a time period of 7 days to 21 days in a vascular environment.

6. A method as in claim 1, wherein the releasing comprises delaying substantial release of methylprednisolone for at least one hour following implantation of the prosthesis.

7. A method as in claim 6, wherein delaying release comprises slowing releasing methylprednisolone from a reservoir with a material that at least partially degrades in a vascular environment over said one hour.

8. A method as in claim 6, wherein delaying release comprises slowing releasing methylprednisolone with a matrix that at least partially degrades in a vascular environment over said one hour.

9. A method as in claim 6, wherein delaying release comprises slowing releasing methylprednisolone with a nondegradable matrix that allows diffusion of methylprednisolone through the nondegradable matrix after said one hour.

10. A method as in claim 6, wherein delaying release comprises slowing releasing methylprednisolone with a rate limiting barrier that allows diffusion of methylprednisolone through the barrier after said one hour.

11. A method as in any one of claims 8–10, wherein the prosthesis is coated with the matrix or barrier by spraying, dipping, deposition, or painting.

12. A method as in claim 1, wherein methylprednisolone is substantially released within a time period of 2 days to 3 months.

13. A method as in claim 1, wherein methylprednisolone and mycophenolic acid are released simultaneously.

14. A method as in claim 1, wherein methylprednisolone and mycophenolic acid are released sequentially.

15. A method for inhibiting restenosis in a blood vessel following recanalization of the blood vessel, said method comprising:
   implanting a vascular prosthesis in the blood vessel; and
   releasing methylprednisolone and mizoribine from the prosthesis when implanted in the blood vessel.

16. A method as in claim 15, wherein methylprednisolone and mizoribine are released simultaneously.

17. A method as in claim 15, wherein methylprednisolone and mizoribine are released sequentially.

18. A method as in claim 15, wherein methylprednisolone is released from the prosthesis at a rate between 5 µg/day to 200 µg/day.

19. A method as in claim 18, wherein methylprednisolone is released at a rate between 10 µg/day to 60 µg/day.

20. A method as in claim 15, wherein methylprednisolone is released from the prosthesis within a time period of 1 day to 45 days in a vascular environment.

21. A method as in claim 20, wherein methylprednisolone is released within a time period of 7 days to 21 days in a vascular environment.

22. A method as in claim 15, wherein the releasing comprises delaying substantial release of methylprednisolone for at least one hour following implantation of the prosthesis.

23. A method as in claim 22, wherein delaying release comprises slowing releasing methylprednisolone from a reservoir with a material that at least partially degrades in a vascular environment over said one hour.

24. A method as in claim 22, wherein delaying release comprises slowing releasing methylprednisolone with a matrix that at least partially degrades in a vascular environment over said one hour.

25. A method as in claim 22, wherein delaying release comprises slowing releasing methylprednisolone with a nondegradable matrix that allows diffusion of methylprednisolone through the nondegradable matrix after said one hour.

26. A method as in claim 22, wherein delaying release comprises slowing releasing methylprednisolone with a rate limiting barrier that allows diffusion of methylprednisolone through the barrier after said one hour.

27. A method as in any one of claims 24–26, wherein the prosthesis is coated with the matrix or barrier by spraying, dipping, deposition, or painting.

28. A method as in claim 15, wherein methylprednisolone is substantially released within a time period of 2 days to 3 months.

* * * * *